United States Patent [19]
Lowry et al.

[11] Patent Number: 5,885,562
[45] Date of Patent: *Mar. 23, 1999

[54] DEODORANT COMPOSITIONS

[75] Inventors: Michael Richard Lowry, Chester; Gordon Robert Wight, Wirral, both of United Kingdom

[73] Assignee: Chesebrough-Pond's USA Co., Division of Conopco, Inc., Greenwich, Conn.

[*] Notice: This patent issued on a continued prosecution application filed under 37 CFR 1.53(d), and is subject to the twenty year patent term provisions of 35 U.S.C. 154(a)(2).

[21] Appl. No.: 626,655

[22] Filed: Apr. 2, 1996

[30] Foreign Application Priority Data

Apr. 3, 1995 [GB] United Kingdom ................. 9506841.7

[51] Int. Cl.⁶ ................................ A61K 7/32; A61K 7/00
[52] U.S. Cl. ................................ 424/65; 424/66; 424/67; 424/68; 424/400; 424/401; 424/DIG. 5
[58] Field of Search ................. 424/65, 66, 67, 424/68, 400, 401, DIG. 5

[56] References Cited

U.S. PATENT DOCUMENTS

| | | | |
|---|---|---|---|
| 3,152,181 | 10/1964 | Shapiro et al. | 424/65 |
| 4,478,821 | 10/1984 | Carrillo | 424/65 |
| 4,818,524 | 4/1989 | Gibbs | 424/76.1 |
| 4,946,672 | 8/1990 | Gibbs | 424/76.1 |
| 5,578,563 | 11/1996 | Trinh et al. | 510/513 |

FOREIGN PATENT DOCUMENTS

| | | |
|---|---|---|
| 1 226 213 | 3/1983 | Canada . |
| 0 180 309 | 5/1986 | European Pat. Off. . |
| 0 252 695 | 1/1988 | European Pat. Off. . |
| 0 450 117 | 10/1991 | European Pat. Off. . |
| 0 507 317 | 10/1992 | European Pat. Off. . |
| 0 640 352 | 3/1995 | European Pat. Off. . |
| 35 37 627 | 11/1984 | Germany . |
| 465 650 | 10/1990 | Sweden . |
| 960 084 | 6/1964 | United Kingdom . |
| 2 298 575 | 3/1996 | United Kingdom . |
| 94/27440 | 9/1994 | WIPO . |

*Primary Examiner*—Shelley A. Dodson
*Attorney, Agent, or Firm*—Milton L. Honig

[57] ABSTRACT

A propellant driven deodorant composition for topical application to the human skin, comprising a deodorant active material comprising a cosmetically acceptable. polyhexamethylene biguanide salt, a cosmetically suitable vehicle comprising a short chain monohydric alcohol, and a non polar propellant composition having a Hildebrand Solubility Parameter of less than 14.5 $MPa^{1/2}$, characterized in that the composition additionally comprises an effective amount of water.

10 Claims, No Drawings

DEODORANT COMPOSITIONS

BACKGROUND OF THE INVENTION

1. Field of the Invention

This invention relates to deodorant compositions, which are suitable for topical application to the human skin. In particular, it refers to propellant driven aerosol compositions which contain certain biguanide compounds.

2. The Related Art

Deodorant compositions suitable for topical application to the human skin, in particular the underarm area, have long been known. These typically comprise a deodorant active material, which may be an inorganic metal salt, such as an aluminium or zinc salt, in a cosmetically acceptable base. Alternatively the deodorant agent in the topical composition may be organic; two very popular and often used organic deodorant agents are ethanol and triclosan. For a propellant driven aerosol product, a base composition containing an appropriate deodorant agent is typically combined in an aerosol can with an appropriate amount of propellant.

Conventional propellant driven aerosol compositions of this form do have associated problems. The exact nature of the problem will vary according to the formulation and the deodorant agent used, but typical problems include insufficient deodorant efficacy, perfume interaction, or sensory problems such as the production of visible deposits.

It is known that certain biguanide salts can have antimicrobial activity. For example, polyhexamethylene biguanide hydrochloride (PHMB) salts have been sold by Zeneca for many years, for example as a 20% aqueous solution of the hydrochloride salt, under the tradename Cosmocil CQ, for purposes which include their use as antimicrobials. In addition, such an effect is described in "Disinfection, Sterilization, and Preservation", chapter 18(polymeric antimicrobial agents),fourth edition, Seymour S. Block, Lea & Febiger, 1991.

Such polyhexamethylene biguanide hydrochloride type materials are also known deodorant actives in their own right. For example in U.S. Pat. No. 4,478,821 (Gillette), the ability of PHMB salts to reduce body odour is described. According to the teaching therein, such salts are suitable for inclusion in any product form, including lotions, sticks, creams, ointments, powders, suspensions, soaps, gels, and pressurized aerosols. However it is noted that no propellant driven aerosol compositions are exemplified in this patent; instead the examples relate to liquid and stick formulations.

However, problems have been experienced in trying to incorporate hydrophilic, cationic polymer type materials, such as PHMB salts, into propellant driven aerosol formulations, to try to formulate compositions which would be suitable for commercial sale. In particular such salts have been found to be incompatible with aerosol formulations which comprise significant amounts of a non polar propellant, such as a hydrocarbon propellant, and short chain monohydric alcohol, such as ethanol.

If the neat PHMB salts are introduced into a hydrocarbon propellant/ethanol system, the salt does not appreciably dissolve. Attempts have been made to incorporate PHMB salts into propellant driven aerosols where the propellant is non polar, using surfactants. However, this has not been found to be an efficient way of dissolving or dispersing the salts into such aerosol compositions, since it has proved difficult to find a surfactant which was compatible with the short chain monohydric alcohol/non polar hydrocarbon vehicle, did not effect the chemical nature of the PHMB salt, and yet was suitable for use in a topical cosmetic composition.

SUMMARY OF THE INVENTION

After much research in the area, we have surprisingly found that PHMB salt materials can be incorporated into propellant driven aerosol products where the propellant is non polar (in particular where the propellant is a hydrocarbon), and where the cosmetic vehicle of the composition contains relatively large amounts of short chain $(C_2-C_6)$monohydric alcohol (in particular ethanol), provided the composition additionally comprises a certain critical amount of water.

DETAILED DESCRIPTION OF THE INVENTION

Thus, according to the first aspect of the invention, there is provided a propellant driven deodorant composition for topical application to the human skin, comprising a deodorant active material comprising a cosmetically acceptable polyhexamethylene biguanide salt, a cosmetically suitable vehicle comprising a short chain monohydric alcohol, and a non polar propellant composition, characterised in that the composition additionally comprises an effective amount of water.

The PHMB salts for use in compositions according to the invention will typically be the protonated form of the following general formula;

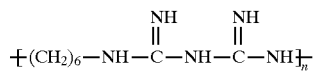

wherein n may have a value of up to about 500 or more, but typically has a value of 1–40, with termination of the polymer chain provided by an appropriate end group (see the Block reference described above). In preferred embodiments of the invention, n has an average value of 10–13; such a cosmetically acceptable PHMB salt is the hydrochloride salt, which can be commercially obtained from Zeneca under the trade name Cosmocil CQ. Preferably, the PHMB salt can be present in compositions according to the invention at a level of 0.01–0.5%, more preferably 0.02–0.1% by weight of the composition, though good results have been found with a level of 0.01–0.05% by weight of PHMB salts in the composition.

Another preferred and commercially available form of PHMB salt is Lonzabac-BG, which has an average value for n of 4–6, and is available from Lonza.

The short chain $(C_2-C_6)$monohydric alcohol for use in compositions according to the invention is preferably ethanol. It may be present in compositions according to the invention at a level of 20–80% by weight of the composition.

The non polar propellant composition for use in compositions according to the invention is preferably a hydrocarbon propellant, such as propane, isopropane, butane, isobutane, pentane, or mixtures thereof. The non polar propellant will have a Hildebrand Solubility Parameter (δ) typically less than about 14.5 $MPa^{1/2}$. The definition of Hildebrand Solubility Parameter can be found in the CRC Handbook of Solubility Parameters and Other Cohesion Parameters, second edition, Allan F. M. Barton, CRC Press, the contents of which is incorporated by reference. The non polar propellant will typically be present in compositions according to the invention at a level of 20–80% by weight of the composition.

It is a preferred aspect of the invention that the ratio of the short chain monohydric alcohol to non polar propellant in the composition is in the region 0.43:1 to 2.33:1, more preferably 0.67:1 to 1.5:1; conveniently the ratio between the two is close to 1:1. The amount of short chain monohydric alcohol and non polar propellant in the composition can be typically as high as 99% by weight of the composition. An effective amount of water present in compositions according to the invention will be sufficient to dissolve or disperse the PHMB salt in the non polar propellant/monohydric alcohol composition, but will be insufficient to phase separate the solvent combination at room temperature (i.e. 22° C.). Typically the amount of water that can be incorporated in compositions according to the invention is in the region of 0.1–6%, preferably approximately 1 to 6%, more preferably approximately 2 to 6% and most preferably approximately 4 to 6% by weight of the composition, where the ratio of short chain monohydric alcohol to non polar propellant is in the region of 1:1. At such levels of water it has been found possible to accommodate in the region of 0.04% by weight of PHMB salt in the composition. If however the ratio of short chain monohydric alcohol to non polar propellant increases to a ratio of 3:1 or more, the amount of water that may be accommodated in the composition may be in the region of 12% by weight, or higher.

It has been found to be a highly advantageous aspect of the invention that the invention contains an effective amount of a polarity modifier. The polarity modifiers for use according to the invention will typically have a Hildebrand Solubility Parameter in the region 14.5–24 $MPa^{1/2}$, more preferably in the region 15–20 $MPa^{1/2}$; it is thought that they may act to allow the non polar propellant/monohydric alcohol base to accommodate more water, thereby improving the tolerance of the base to the PHMB salt. The presence of a polarity modifier is particularly preferred when the level of PHMB salt in the composition is greater than about 0.02% by weight.

Polarity modifiers for use in compositions according to the invention include $C_{10}$–$C_6$ monohydric and aliphatic alcohols, including dodecanol, decanol, myristyl alcohol, and cetyl alcohol; branched chain alcohols such as isodecanol (e.g. ISOFOL 12, ex. Croda) and isopropanol; ethers such as 1-(2-ethyl hexyl) glycerol ether (e.g. SENSIVA SC50, ex. Schulke & Mayr), dipropylene glycol methyl ethers (e.g. DOWANOL DPM, ex. Dow Corning), and polypropylene glycol ethers (e.g UCON 50-HB-660, ex. Union Carbide); ketones such as acetone; emollient solvents such as ARLAMOL E (ex. Atlas); or esters, such as diethyl phthalate. Particularly preferred is dodecanol.

Preferably, the polarity modifier can be present at levels of up to about 50% by weight of the composition, depending on the ratio of the short chain monohydric alcohol to non polar propellant, but is more typically present in the composition at a level of 1–15% by weight of the composition.

In the presence of the polarity modifier, the level of water that may be present in compositions according to the invention is significantly increased, and may be up to about 10% by weight, where the short chain monohydric alcohol and non polar propellant are present in roughly equal amounts. The amount of PHMB salt that may be incorporated in compositions according to the invention is up to about 0.5% by weight of the composition.

Particularly preferred polarity modifiers for use in compositions according to the invention are those which can solubilise at least 5% by weight of water into a test solution comprising hexane, ethanol and the polarity modifier, in the ratios 45:45:10, at 22° C., without causing phase separation of the solution.

A further approach to trying to provide stable propellant driven aerosol compositions containing PHMB salt has been to modify the polarity of the non polar propellant element of the composition. This can be done by total or partial substitution of the non polar propellant with a propellant which is more polar.

Thus, according to a further aspect of the invention, there is provided a propellant driven aerosol composition for topical application to the human skin, comprising a deodorant material comprising a cosmetically acceptable polyhexamethylene biguanide salt, a cosmetically suitable vehicle comprising a short chain monohydric alcohol, an effective amount of water, and a propellant composition containing a propellant which has a Hildebrand Solubility Parameter in the region 14.5–20 $MPa^{1/2}$, more preferably in the region 16–19 $MPa^{1/2}$.

Such compositions can conveniently be free of non polar propellants, such as the hydrocarbon propellants described above.

Alternatively, the propellant having a Hildebrand Solubility Parameter of 14.5–20 $MPa^{1/2}$ may be present in such compositions at a level of up to about 90% or more, more preferably 5–80% by weight of the composition.

A particularly preferred category of propellant for use according to this aspect of the invention are ethers, for example diethyl ether, dimethoxy ethane (e.g. Methylal, ex. Lambiotte & Gie), and in particular dimethyl ether (which has a Hildebrand Solubility Parameter of 18 $MPa^{1/2}$).

Propellant driven aerosol compositions according to the invention may additionally comprise other materials. These include;

volatile and non volatile silicones, such as dimethyl cyclosiloxanes or polydimethyl siloxane, e.g., DOW CORNING fluids DC244, DC245, DC344, DC345, Q2 1465 and the 200 fluids;

deodorant active perfumes, and deodorant compounds which can act as antimicrobial agents;

hydrophobic oils, such as liquid paraffin oils, isopropyl palmitate, and other emollients;

thickeners such as hydroxypropyl celluloses, for example Klucel;

perfumes;

preservatives and antioxidants;

skin benefit agents, such as allantoin;

other cosmetic adjuncts conventionally employed in propellant driven aerosol products.

EXAMPLES

The inventions will now be further described by way of example only.

Examples 1–3

The following compositions were prepared, and observed at room temperature to see firstly whether the PHMB salt in the composition remains dissolved or dispersed (i.e. did a precipitate of PHMB salt form?), and secondly whether the resulting solution remained in one phase, or separated to form two liquid phases.

Example 1

| Component | % by weight | | |
|---|---|---|---|
| Ethanol (1) | 58.4 | 52.9 | 48.4 |
| Propellant CAP48 (2) | 40.0 | 40.0 | 40.0 |

-continued

| Component | % by weight | | |
|---|---|---|---|
| Water | — | 5.5 | 10.0 |
| Cosmocil CQ (3) | 0.1 | 0.1 | 0.1 |
| Perfume | 1.5 | 1.5 | 1.5 |
| Phase description | | | |
| Polymer precipitation | Yes | No | No |
| Number of liquid phases | 1 | 1 | 2 |

Notes:
(1) DEB 100
(2) Propane/iso-butane/butane blend ex Calor
(3) 20% aqueous solution, PHMB ex Zeneca

Example 2

| Component | % by weight | |
|---|---|---|
| Ethanol (1) | 52.25 | 41.8 |
| Propellant CAP48 (2) | 40.0 | 40.6 |
| Dodecanol (3) | — | 9.9 |
| Water | 7.5 | 7.43 |
| Cosmocil CQ (4) | 0.25 | 0.27 |
| Phase description | | |
| Polymer precipitation | No | No |
| Number of liquid phases | 2 | 1 |

Notes:
(1) DEB 100
(2) Propane/iso-butane/butane blend ex Calor
(3) Ex BDH
(4) 20% aqueous solution, PHMB ex Zeneca

Example 3

| Component | % by weight | |
|---|---|---|
| Ethanol (1) | 36.5 | 36.5 |
| Propellant CAP48 (2) | 45.0 | — |
| Propellant DME (3) | — | 45.0 |
| Water | 17.5 | 17.5 |
| Cosmocil CQ (4) | 1.0 | 1.0 |
| Phase description | | |
| Polymer precipitation | No | No |
| Number of liquid phases | 2 | 1 |

Notes:
(1) DEB 100
(2) Propane/iso-butane/butane blend ex Calor
(3) Dimethyl ether ex Conoco
(4) 20% PHMB aqueous solution ex Zeneca

Example 4

The following compositions were prepared to demonstrate the increasing clarity and decreasing precipitation and turbidity with increasing levels of water

| | % by weight | | | | | | | |
|---|---|---|---|---|---|---|---|---|
| Ethanol (1) | 58.4 | 57.4 | 56.4 | 55.4 | 54.4 | 53.4 | 52.4 | 51.4 |
| Propellant CAP48 (2) | 40 | 40 | 40 | 40 | 40 | 40 | 40 | 40 |
| Water | 0 | 1 | 2 | 3 | 4 | 5 | 6 | 7 |
| Cosmocil CQ (4) | 0.1 | 0.1 | 0.1 | 0.1 | 0.1 | 0.1 | 0.1 | 0.1 |
| PERFUME | 1.5 | 1.5 | 1.5 | 1.5 | 1.5 | 1.5 | 1.5 | 1.5 |
| Appearance: | ppt | xxx | xx | x | L | L | L | 2L | key:
ppt = precipitate
xxx = turbid liquid
xx = slightly turbid liquid
x = very slightly turbid liquid
L = clear liquid
2L = 2 clear liquid phases

Examples 5–10

The following compositions are illustrative of deodorant compositions suitable for topical use, according to the invention

Example 5

| Component | % by weight |
|---|---|
| Ethanol (1) | 52.9 |
| Propellant CAP48 (2) | 40.0 |
| Water | 5.5 |
| Cosmocil CQ (3) | 0.1 |
| Perfume | 1.5 |

Notes:
(1) DEB 100
(2) Propane/iso-butane/butane blend ex Calor
(3) 20% aqueous solution PHMB ex Zeneca

Example 6

| Component | % by weight |
|---|---|
| Ethanol (1) | 40.75 |
| Propellant CAP48 (2) | 40.0 |
| Water | 7.5 |
| Cosmocil CQ (3) | 0.25 |
| Dodecanol (4) | 10.0 |
| Perfume | 1.5 |

Notes:
(1) DEB 100
(2) Propane/iso-butane/butane blend ex Calor
(3) 20% aqueous solution, PHMB ex Zeneca
(4) ex BDH

Example 7

| Component | % by weight |
|---|---|
| Ethanol (1) | 42.9 |
| Propellant CAP48 (2) | 40.0 |
| Water | 5.5 |
| Cosmocil CQ (3) | 0.1 |
| Iso-propanol (4) | 10.0 |
| Perfume | 1.5 |

Notes:
(1) DEB 100
(2) Propane/iso-butane/butane blend ex Calor
(3) 20% aqueous solution, PHMB ex Zeneca
(4) ex BDH

Example 8

| Component | % by weight |
| --- | --- |
| Ethanol (1) | 39.5 |
| Propellant CAP30 (2) | 20.0 |
| Propellant DME (3) | 28.0 |
| Water | 10.0 |
| Cosmocil CQ (4) | 0.5 |
| Cremaphor RH410 (5) | 0.5 |
| Perfume | 1.5 |

Notes:
(1) DEB 100
(2) Propane/iso-butane/butane blend ex Calor
(3) Dimethyl ether ex Conoco
(4) 20% aqueous solution, PHMB ex Zeneca
(5) Polyoxyethylene (45) hydrogenated castor oil ex BASF

Example 9

| Component | % by weight |
| --- | --- |
| Ethanol (1) | 39.0 |
| Propellant CAP30 (2) | 20.0 |
| Propellant DME (3) | 28.0 |
| Water | 10.0 |
| Cosmocil CQ (4) | 1.0 |
| Cremaphor RH410 (5) | 0.5 |
| Perfume | 1.5 |

Notes:
(1) DEB 100
(2) Propane/iso-butane/butane blend ex Calor
(3) Dimethyl ether ex Conoco
(4) 20% aqueous solution, PHMB ex Zeneca
(5) Polyoxyethylene (45) hydrogenated castor oil ex BASF

Example 10

| Component | % by weight |
| --- | --- |
| Ethanol (1) | 34.25 |
| Propellant DME (2) | 45.0 |
| Water | 17.5 |
| Cosmocil CQ (3) | 1.0 |
| Isopropyl Myristate (4) | 0.25 |
| Cremaphor RH410 (5) | 0.5 |
| Perfume | 1.5 |

Notes:
(1) DEB 100
(2) Dimethylether ex Conoco
(3) 20% aqueous Solution, PHMB ex Zeneca
(4) Estol 1514 ex Unichema
(5) Polyoxyethylene (45) hydrogenated castor oil ex BASF

We claim:

1. A propellant driven deodorant composition for topical application to the human skin comprising:
   (i) from 0.01 to 0.5% by weight of a cosmetically acceptable polyhexamethylene biguanide salt;
   (ii) from 20 to 80% by weight of a $C_2$–$C_6$ monohydric alcohol;
   (iii) from 20 to 80% by weight of a non-polar propellant composition having a Hildebrand Solubility Parameter of less than 14.5 $MPa^{1/2}$ comprising at least one hydrocarbon; and
   (iv) from 0.1 to 6% by weight of water.

2. A deodorant composition according to claim 1, additionally comprising a propellant having a Hildebrand Solubility parameter of 14.5–20 $MPa^{1/2}$.

3. A deodorant composition according to claim 1, wherein the ratio of the monohydric alcohol to the propellant is in the region 0.43:1–2.33:1.

4. A deodorant composition according to claim 1, wherein the composition additionally comprises a polarity modifier.

5. A deodorant composition according to claim 4, wherein the polarity modifier is present at a level of 1–15% by weight of the composition.

6. A deodorant composition according to claim 4, wherein the polarity modifier has a Hildebrand Solubility Parameter of 14.5–20 $MPa^{1/2}$.

7. A deodorant composition according to claim 1, wherein the polarity modifier is a $C_{10}$–$C_{16}$ monohydric or aliphatic alcohol.

8. A deodorant composition according to claim 7 wherein the polarity modifier is selected from the group consisting of a $C_{12}$ aliphatic alcohol, a branched chain alcohol, an ether, a ketone, an emollient solvent and an ester.

9. A deodorant composition according to claim 7 wherein the polarity modifier is dodecanol.

10. A propellant driven deodorant composition for topical application to the human skin comprising:
    (i) from 0.01 to 0.5% by weight of a cosmetically acceptable polyhexamethylene biguanide salt;
    (ii) from 20 to 80% by weight of a $C_2$–$C_6$ monohydric alcohol;
    (iii) from 20 to 80% by weight of a propellant composition having a Hildebrand Solubility Parameter of 14.5 to 20 $MPa^{1/2}$ comprising dimethyl ether; and
    (iv) from 0.1 to 17.5% by weight of water.

* * * * *